United States Patent [19]
Kim

[11] Patent Number: 6,037,464
[45] Date of Patent: Mar. 14, 2000

[54] METHOD FOR THE EXTRACTION OF GENOMIC DNA FROM FISH BLOOD OR SPERM

[76] Inventor: Dong-Soo Kim, Research Center for Ocean Industrial Development National Fisheries University of Pusan, #599-1 Taeyun-3-dong, Nam-gu, Pusan 608-737, Rep. of Korea

[21] Appl. No.: 08/534,531

[22] Filed: Sep. 27, 1995

[51] Int. Cl.[7] .............................. C07H 1/00; C07H 21/04
[52] U.S. Cl. ...................................... 536/25.42; 536/25.41
[58] Field of Search ............................... 536/25.41, 25.42

[56] References Cited

PUBLICATIONS

Brem et al., Aquaculture, 68: 209–219, 1988.
Dunham et al., Trans. Am. Fish Soc., 116: 87–91, 1987.
Ivics et al., Mol. Marine Biol. Biotechnol., 2: 162–173, 1993.
Khoo et al., Aquaculture, 107: 1–19, 1992.
Penman et al., Aquaculture, 85: 35–50, 1990.
Penman et al., Mol. Repr. Dev., 30: 201–206, 1991.
Zhang et al., Mol. Repr. Dev., 25: 3–13, 1990.
Taggart et al., J. Fish Biol. 40: 963–965, 1992.
Cummings et al., Biotechniques, 17(3): 426–430, 1994.

*Primary Examiner*—Gary L. Kunz
*Attorney, Agent, or Firm*—Anderson Kill Olick PC

[57] ABSTRACT

A simple and efficient process for the extraction of genomic DNA from a fish, requiring a minuscule amount of blood or sperm from the fish without sacrificing it, comprises: adding blood or semen taken from the fish into a first buffer for cell-lysis to create a first suspension; centrifuging the first suspension to collect a precipitated nuclear pellet; adding the precipitated pellet into a second buffer for nuclear-lysis to create a second suspension; and extracting DNA from the second suspension.

4 Claims, 2 Drawing Sheets

METHOD FOR THE EXTRACTION OF GENOMIC DNA FROM FISH BLOOD OR SPERM

FIELD OF THE INVENTION

The present invention relates to a process for the extraction of genomic DNA from fish blood or sperm; and, more particularly, it pertains to a simple and efficient process for the extraction of genomic DNA that requires a limited amount of blood or sperm from fish without sacrificing it.

BACKGROUND OF THE INVENTION

Recent progress made in the studies on piscine genes has developed various techniques for the extraction of genomic DNA from fish.

One of such techniques is to extract DNA from fish liver, fin or muscle, or even the whole body of small fish, which is based on the technique developed for mammals(see Brem, G. B., et al., *Aquaculture*, 68, 209–219(1988); Dunham, R. A., et al., *Trans. Am. Fish Soc.*, 116, 87–91(1987); Ivics, Z., et al., *Mol. Marine Biol. Biotechnol.*, 2, 162–173(1993); Khoo, H. W., et al., *Aquaculture*, 107, 1–19(1992); Penman, D. J., et al., *Aquaculture*, 85, 35–50(1990); Penman, D. J., et al., *Mol. Repr. Dev.*, 30, 201–206(1991); and Zhang, P., et al., *Mol. Repr. Dev.*, 25, 3–13(1990)). Another process developed for extracting DNA from salmonid fish is also based on the technique for mammals(see Taggart, J. B., et al., *J. Fish Biol.*, 40, 963–965(1992)). However, these techniques are very complicated and require expensive proteinases, RNases, thermostatic apparatus, and a great deal of labor. Therefore, the analysis of large number of samples may be tiresome, laborious, and not economical in many situations. Further, fish is inevitably sacrificed or injured seriously in case of these methods.

A method for extracting genomic DNA from fish blood or sperm has been recently developed for the purpose of DNA fingerprinting(Cummings, S. A. and G. H. Thorgaard, *Biotechniques*, 17(3), 426–430(1994)). In this process, blood is obtained from the heart of an anesthetized salmon by using a syringe containing 1×SSC(0.15M NaCl, 0.015M sodium citrate) and the blood sample so obtained is put into a tube. A large amount of distilled water is added to the tube to disrupt the cells, and then, 5×SSC is added to make the solution isotonic. The mixture is centrifuged to obtain precipitate, which is washed with NaCl and EDTA, and then centrifuged again to obtain precipitate. A buffer solution containing proteinase K is added to the precipitate and the mixture is stirred at 60° C. overnight to digest the precipitate. The mixture is cooled to a room temperature and ethanol is added to precipitate DNA, which is then separated and washed with ethanol. The obtained DNA is dried and dissolved in 1×TE buffer at 37° C. overnight. In case of sperm, a buffer solution containing proteinase K is added and the mixture is maintained at 60° C. overnight to digest the sperm; and then the same procedures as in the case of blood are repeated.

However, in this process, expensive proteinase K is employed for the extraction of DNA, which in turn requires a thermostatic apparatus and a stirrer. Further, it takes a long time to complete the process. More importantly, a considerable amount of proteins may precipitate together with DNA during the process.

Therefore, efforts have continued for the development of a simple and economical process for the extraction of genomic DNA from fish.

SUMMARY OF THE INVENTION

Accordingly, it is a primary object of the present invention to provide a simple and economical process for the extraction of genomic DNA having a high purity from fish without sacrificing the latter.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1:
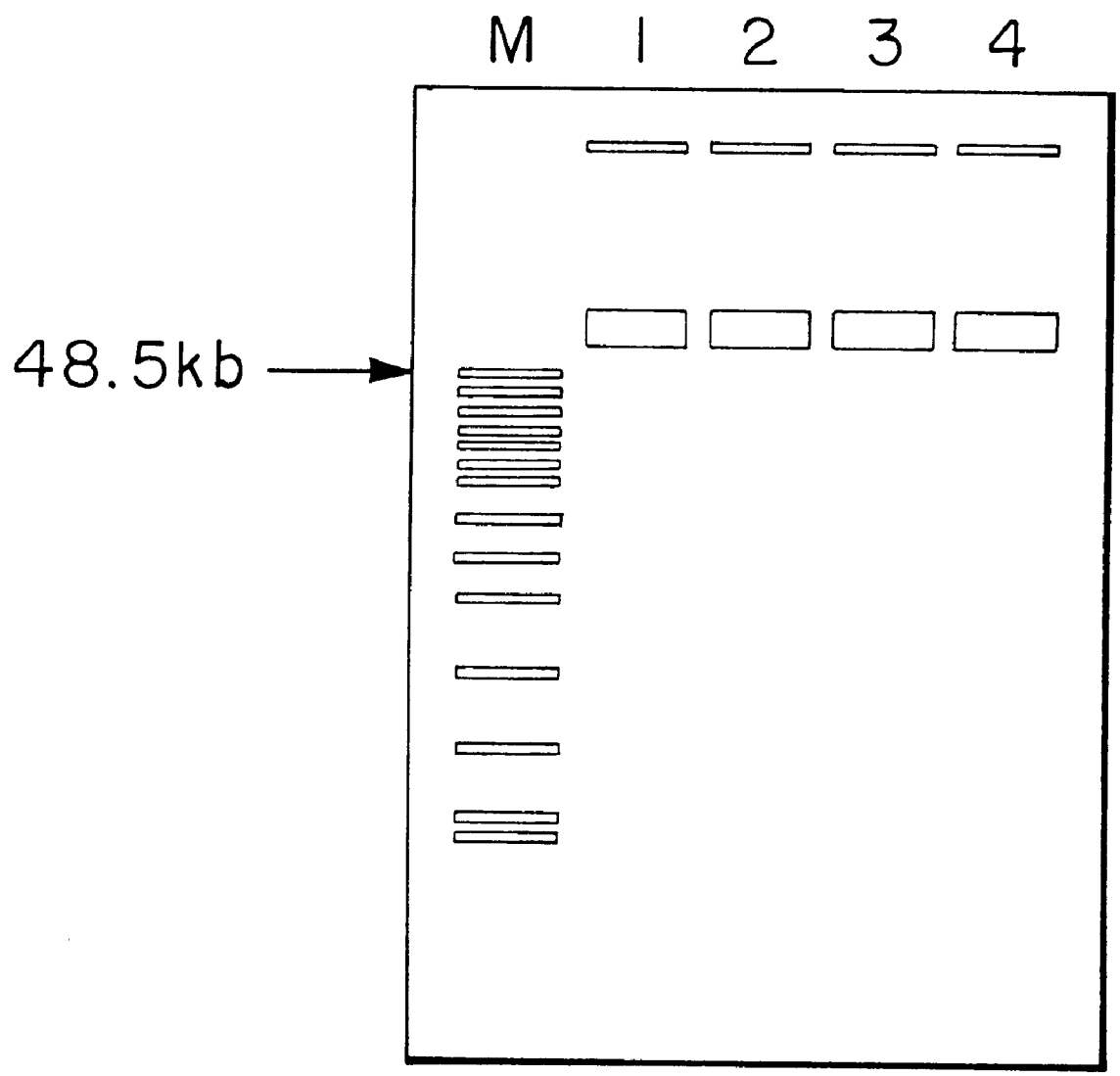
FIG. 1 shows the result of agarose gel electrophoresis for verifying the purity of the DNA samples extracted from nile tilapia(*Oreochromis niloticus*) and mud loach(*Misgurnus mizolepis*) in accordance with the inventive process.

All references cited herein are hereby incorporated in their entirety by reference.

The process of the present invention requires only a small amount of blood or semen from fishes, for example, 5 to 10 $\mu l$ of blood or 1 to 2 $\mu l$ of semen. The blood or semen sample is added to a first buffer for cell-lysis to create a first suspension.

The first buffer for cell-lysis consists essentially of a surfactant for lysing a cell membrane, for example, Triton X-100 in a concentration ranging from 1 to 5%, preferably, 2.5%. An exemplary buffer may consist of 12.5 mM citric acid, 25 mM sodium citrate, 41 mM dextrose, and 2.5% Triton X-100. The buffer, owing to the characteristic of the surfactant therein, disrupts only the cell membrane without disrupting nuclear membrane, which may be completed within 2 or 3 seconds only.

After disrupting the cell membrane, the first suspension is centrifuged at a gravity ranging from 1,800 to 2,000 g for a time period ranging from 5 to 10 minutes to precipitate the nuclear pellet. The nuclear pellet collected is resuspended using a gentle vortexing, and a second buffer for nuclearlysis is added to create the second suspension.

The second buffer for nuclear-lysis preferably comprises sodium dodecyl sulfate(SDS) in a concentration ranging from 0.1 to 1.0%, preferably, 0.5%. A representative buffer may consist of 10 mM Tris-Cl, 1 mM EDTA, 0.5 M NaCl, and 0.5% SDS. pH of the buffer ranges from 6.8 to 8.5, preferably, 8.0. The reaction of the buffer to the nuclear pellet may be completed within 5 to 10 seconds.

The above procedures do not require any particular temperature control, and can be carried out at a room temperature without restriction.

After the lysis of the nuclear membrane, the second suspension is extracted using organic solvent and the organic layer is centrifuged to obtain a supernatant containing DNA. An exemplary organic solvent which may be used for the extraction is Tris-saturated phenol(pH 8.0). The supernatant is further treated with another organic solvent, e.g., phenol:chloroform mixture(1:1(v/v)), in accordance with the same procedure as above to obtain a supernatant. To the supernatant is added isopropanol to precipitate DNA, and then the precipitated DNA is recovered from the solution and dissolved in 1×TE buffer for a direct use in the genetic analysis.

The buffer for the cell-lysis or nuclear-lysis used in the present invention is stable at a room temperature and has long-term storage life. Further, since the present invention employs only the collected nuclei for the DNA extraction and not the whole cell, it is not required to remove a large amount of proteins; and, therefore, a simple extraction will be sufficient to remove residual proteins. In addition, unlike the prior art processes, expensive RNase is not needed since the removal of cellular RNA, which is usually present in the cytoplasm, is unnecessary. The present invention employs isopropanol which is much more effective than ethanol in precipitating DNA, and, therefore, relatively small amount thereof is sufficient to precipitate DNA in the supernatant even at a room temperature.

The following Examples are intended to further illustrate the present invention without limiting its scope.

EXAMPLE 1

Ten $\mu$l of blood($1.5 \times 10^7$ cells) was collected from a nile tilapia(*Oreochromis niloticus*) by using a capillary or disposable syringe. 1,200 $\mu$l of buffer for cell-lysis(12.5 mM citric acid, 25 mM sodium citrate, 41 mM dextrose, 2.5% Triton X-100) was added to the blood, and mixed thoroughly for 5 seconds. The mixture was microcentrifuged at 2,500 rpm for 10 minutes to collect nuclear pellet.

The collected nuclear pellet was subjected to a gentle vortexing, and 600 $\mu$l of a buffer for nuclear-lysis(10 mM Tris-Cl, 1 mM EDTA, 0.5 M NaCl, 0.5% SDS, pH 8.0) was added. The suspension was mixed slowly for 10 seconds. To the mixture was added an equal amount of Tris-saturated phenol(pH 8.0), and the resultant was mixed for 10 seconds and then centrifuged at 14,000 rpm for 3 minutes to obtain a supernatant. An equal amount of phenol:chloroform mixture(1:1(v/v)) was added to the supernatant and the above procedures were repeated to obtain a supernatant.

To the supernatant was added an equal amount of isopropanol to precipitate DNA. The precipitated DNA is recovered from the solution and dissolved in 100 $\mu$l of 1xTE buffer(10 mM Tris, 1 mM EDTA, pH 8.0).

The O.D.(optical density) value of the resulting solution was measured at 260 nm and 280 nm by using a UV-Vis spectrophotometer. The amount of DNA in the solution can be calculated from the O.D. value at 260 nm($OD_{260}$), in accordance with the method described by Sambrook et al. in *Molecular Cloning: A Laboratory Manual*, 2nd Ed., 3, Appendix E.5, wherein it is described that an $OD_{260nm}$ of 1.0 corresponds to approximately 50 $\mu$g/ml for double-stranded DNA. As the $OD_{260}$ value of the resulting solution was measured as 6.01, the concentration of DNA therein was calculated as about 301 $\mu$g/ml, and the amount of DNA in 100 $\mu$l of the solution was determined as 30.1 $\mu$g. Considering the genome size of nile tilapia(2.6 pg of DNA/cell; Brem, et al., *Aquaculture*, 68, 209–219(1988)) and the number of cells used in the experiment, the yield of DNA was calculated as about 77%.

Further, the purity of the extracted DNA was determined from the $OD_{280}$ value of the DNA solution, in accordance with the method described by Sambrook et al., supra, wherein it is described that pure DNA has an $OD_{260}/OD_{280}$ value of 1.8. As the $OD_{280}$ value of the resulting DNA solution was measured as 3.31, the $OD_{260}/OD_{280}$ value was calculated therefrom as 1.81 and, therefore, it was confirmed that the extracted DNA was pure.

EXAMPLE 2

The same procedures as in Example 1 were repeated by using 1 $\mu$l of semen($3 \times 10^7$ cells) from nile tilapia instead of 10 $\mu$l of blood. The yield of DNA was also about 75% and the extracted DNA was pure.

EXAMPLE 3

For the purpose of confirming the purity of DNA obtained in Example 1, an agarose gel electrophoresis was carried out as follows.

DNA solutions comprising the genomic DNA of nile tilapia and loach in TE buffer were prepared in accordance with the same procedures as in Example 1, and parts of them were left alone at 37° C. for 3 hours if the residual activity of DNase were completely removed.

Four kinds of DNA samples prepared in the above were loaded onto the top of 0.4% TAE/agarose gel and then subjected to an electrophoresis at 30 volts for 8 hours. The result is shown in FIG. 1.

In FIG. 1, lane M shows a standard DNA size marker(high molecular weight DNA marker, Gibco BRL);

lanes 1 and 2 represent DNA samples in TE buffer, extracted from the blood of nile tilapia in accordance with the process of the present invention, before and after being left alone, respectively; and lanes 3 and 4 display DNA samples in TE buffer, extracted from the blood of mud loach(*Misgurnus mizolepis*) in accordance with the process of the present invention, before and after being left alone, respectively.

As can be seen from FIG. 1, pure high molecular weight DNAs could be obtained without any degradation.

EXAMPLE 4

For the purpose of confirming that the process of the present invention is applicable to other species of fish equally, the same procedures as described in Example 1 were repeated to extract DNAs from various species of fish.

The DNA samples extracted from various fish using the procedures described in Example 1 and a DNA sample extracted from nile tilapia by using the method described by Cummings and Thorgaard as a comparative sample were subjected to agarose gel electrophoresis. DNA samples were loaded onto the 0.4% TAE/agarose gel and electrophoresed at 30 Volts for 3 hours, and the result is shown in FIG. 2.

Figure 2:
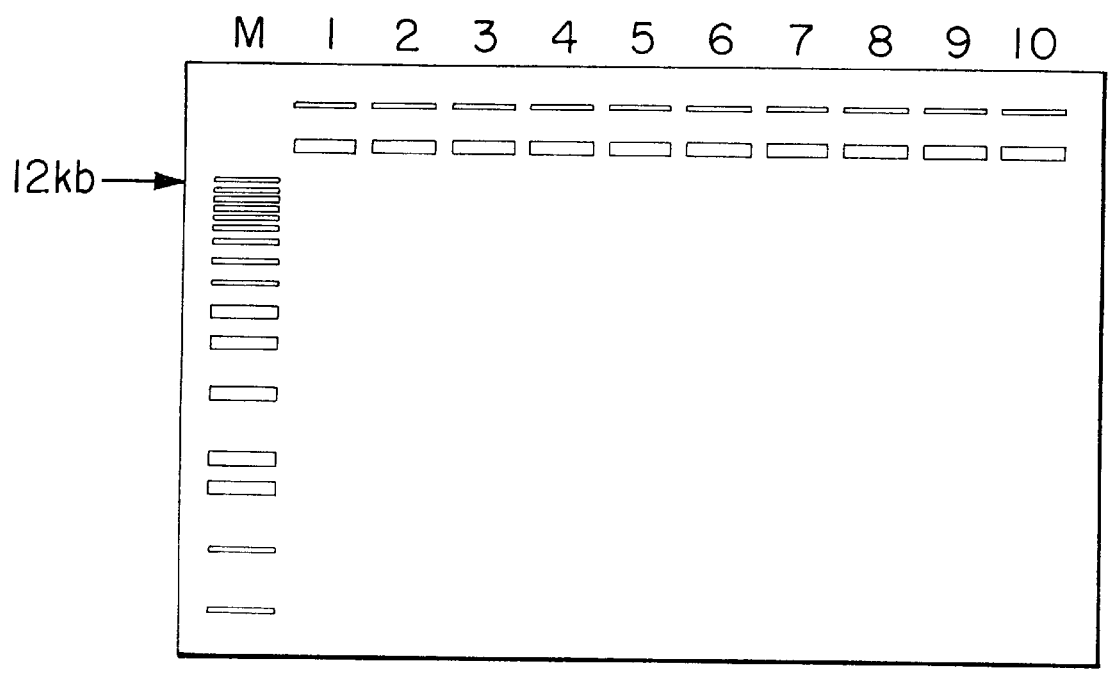
FIG. 2 represents the result of agarose gel electrophoresis by using the DNA samples extracted from various fish species in accordance with the process of the present invention and the DNA sample extracted from blood of nile tilapia using the process of Cummings and Thogaard, supra.

In FIG. 2, lane M shows a standard DNA size marker(1 kb ladder);

lane 1 describes a DNA sample(200 ng) extracted from the blood of nile tilapia(*Oreochromis niloticus*) in accordance with the process of Example 1;

lane 2 depicts a DNA sample(200 ng) extracted from the blood of nile tilapia(*Oreochromis niloticus*) in accordance with the method of Cummings and Thorgaard;

lane 3 provides a DNA sample(500 ng) extracted from the blood of mud loach(*Misgurnus mizolepis*) in accordance with the process of Example 1;

lane 4 offers a DNA sample(500 ng) extracted from the blood of channel catfish(*Ictalurus punctatus*) in accordance with the process of Example 1;

lane 5 presents a DNA sample(1 $\mu$g) extracted from the semen of carp(*Cyprinus carpio*) in accordance with the process of Example 1;

lane 6 illustrates a DNA sample(1 $\mu$g) extracted from the blood of rainbow trout(*Oncorhynchus mykiss*) in accordance with the process of Example 1;

lane 7 displays a DNA sample(200 ng) extracted from the semen of flounder(*Olivaceus paralichthys*) in accordance with the process of Example 1;

lane 8 indicates a DNA sample(100 ng) extracted from the blood of spotted halibut(*Verasper variegatus*) in accordance with the process of Example 1;

lane 9 exhibits a DNA sample(500 ng) extracted from the blood of goldfish(*Carassius auratus*) in accordance with the process of Example 1;

lane 10 gives a DNA sample(100 ng) extracted from the blood of Japanese medaka(*Oryzias latipes*) in accordance with the process of Example 1.

As can be seen from FIG. 2, the process of the present invention is useful for the extraction of genomic DNA with a high purity from a minuscule amount of blood or semen of various fish species including nile tilapia.

What is claimed is:

1. A process for the extraction of genomic DNA from a fish which comprises the steps of:

(a) adding blood or semen taken from the fish into a first buffer for cell-lysis to create a first suspension;

(b) centrifuging the first suspension to collect a precipitated pellet;

(c) adding the precipitated pellet into a second buffer containing no proteinase for nuclear-lysis to create a second suspension; and (d) extracting DNA from the second suspension with an organic solvent.

2. The process of claim 1 wherein said step (d) includes the steps of:

(i) adding an equal amount of Tris-saturated phenol(pH 8.0) to the second suspension and centrifuging the resulting mixture to obtain a first supernatant;

(ii) adding an equal amount of phenol:chloroform mixture (1:1(v/v)) to the first supernatant and centrifuging the resulting mixture to obtain a second supernatant;

(iii) adding an equal amount of isopropanol to the second supernatant to precipitate DNA; and (iv) recovering the precipitated DNA.

3. The process of claim 1 wherein the first buffer for cell-lysis comprises Triton X-100 in a concentration ranging from 1 to 5%.

4. The process of claim 1 wherein the second buffer for nuclear-lysis comprises sodium dodecyl sulfate in a concentration ranging from 0.1 to 1%.

* * * * *